United States Patent [19]

Lehner, II

[11] Patent Number: 5,178,622
[45] Date of Patent: Jan. 12, 1993

[54] INSTRUMENT FOR IMPLANTING A SOFT INTRAOCULAR LENS

[76] Inventor: Robert H. Lehner, II, 3907 Lighthouse Drive, Racine, Wis. 53402

[21] Appl. No.: 786,398

[22] Filed: Nov. 1, 1991

[51] Int. Cl.$^5$ ............................................. A61F 9/00
[52] U.S. Cl. ............................... 606/107; 606/205; 606/207; 606/210; 606/211; 623/6
[58] Field of Search ............... 606/107, 133, 205, 206, 606/207, 208, 209, 210, 211; 623/6

[56] References Cited

U.S. PATENT DOCUMENTS

| | | | |
|---|---|---|---|
| 1,537,793 | 5/1925 | Bates . | |
| 4,124,905 | 11/1978 | Clark | 606/107 |
| 4,190,049 | 2/1980 | Hager et al. | 606/107 |
| 4,198,980 | 4/1980 | Clark . | |
| 4,257,406 | 3/1981 | Schenk | 606/107 |
| 4,750,498 | 6/1988 | Graham . | |
| 4,759,359 | 7/1988 | Willis et al. . | |
| 4,763,650 | 8/1988 | Hauser | 606/107 |
| 4,785,810 | 11/1988 | Baccala et al. . | |
| 4,791,924 | 12/1988 | Kelman . | |
| 4,813,957 | 5/1989 | McDonald | 623/6 |
| 4,836,201 | 6/1989 | Patton et al. | 606/107 |
| 4,844,065 | 7/1989 | Faulkner . | |
| 4,888,015 | 12/1989 | Domino | 623/6 |
| 4,906,247 | 3/1990 | Fritch | 623/6 |
| 4,934,363 | 6/1990 | Smith et al. | 606/107 |
| 4,950,289 | 8/1990 | Krasner | 606/107 |
| 4,955,889 | 9/1990 | Van Gent | 606/107 |
| 4,957,505 | 9/1990 | McDonald | 623/6 |
| 4,959,070 | 9/1990 | McDonald | 623/6 |
| 5,007,913 | 4/1991 | Dulebohn et al. | 606/107 |
| 5,026,393 | 6/1991 | Mackool | 623/6 |
| 5,098,439 | 3/1992 | Hill et al. | 606/107 |

FOREIGN PATENT DOCUMENTS

| | | | |
|---|---|---|---|
| 0639547 | 2/1979 | U.S.S.R. | 606/107 |
| 113482 | 2/1918 | United Kingdom . | |

OTHER PUBLICATIONS

Softrans Elastic Lens Injector Broachure.
Ocular Surgery News; Jul. 15, 1990; Implant Techniques, by: Brooks J. Poley, M.D.
Ocular Surgery News, Dec. 15, 1990, Surgical Maneuver, by: Robert H. Lehner, Jr., M.D.
Ocular Surgery News, Oct. 1, 1991; Small Incision Lenses: technology takes off, by: Leslie Bendra Sabbagh.

*Primary Examiner*—Stephen C. Pellegrino
*Assistant Examiner*—Glenn K. Dawson
*Attorney, Agent, or Firm*—Jansson & Shupe, Ltd.

[57] ABSTRACT

The inventive instrument is an improvement in a surgical instrument of the type having fingers to grasp a soft, foldable intraocular lens (IOL) for implantation in a human eye following removal of the cataractous lens. The IOL has a relatively thick optic body and a relatively thin optic edge having a contour. Each instrument finger is shaped to generally conform to such contour and contact the IOL along the thin edge. The combined thickness of the fingers and the thin edge is no greater than the thickness of the body of the folded IOL. For an IOL of the type having a circular contour, the fingers are crescent-shaped. The IOL may thereby be easily implanted through a narrower incision including such an incision of the scleral tunnel type.

13 Claims, 8 Drawing Sheets

INSTRUMENT FOR IMPLANTING A SOFT INTRAOCULAR LENS

FIELD OF THE INVENTION

This invention is related generally to cataract surgery and, more particularly, to an improved instrument for artificial lens implantation following removal of the cataractous lens.

BACKGROUND OF THE INVENTION

A cataract is the clouding of the natural lens of the eye. In decades past, persons affected with cataracts were treated by removing the cataractous lens tissue and after a suitable recovery period, fitting the patient with thick glasses. While such glasses were conventionally worn, they were often distinctly unconventional in appearance. Some critics describe them as having a thickness approximating that of the bottom of a soft drink bottle. They caused a great deal of distortion to a patients vision.

A relatively recent (and more informed) treatment involves implantation of an artificial intraocular lens (IOL) into the eye after the removal of the cataractous natural lens. The natural lens of the eye is a convex lens which is thicker in the center and thinner on the edges. The IOLs used to replace the natural lens are likewise convex lens which are thicker in the center and thinner on the edges. The thickness varies depending upon the power of the lens and the index of refraction of the material used to produce it. IOLs of the same power can be manufactured with the convexity entirely on one side of the lens or split in various combinations between the two sides. IOLs consist of two basic parts: the "optic" portion which bends the light to produce the focusing power of the lens, and the "haptic" which is the non-optical carrier portion supporting the IOL in the eye. The optic portion of IOLs are usually circular or elliptical. The haptic portions have been produced with a very wide variety of shapes and configurations.

Older cataract extraction techniques involve the removal of the clouded natural lens as a whole or in large pieces. This necessitates a relatively long (perhaps 10 mm or more) incision through the wall of the eye. Commonly such an incision is a "plunge" wound, the depth of which is generally perpendicular to the eyeball wall. Such procedures are characterized by a number of disadvantages. Large incisions require sutures, cause discomfort and have a long healing time before return to normal activities.

Another now commonly used technique for cataract extraction is by phacoemulsification which uses ultrasonic vibration fragmentation and aspiration. This allows the removal of the cataract through a small incision only about 3 mm long.

The IOLs which were first developed were made of hard materials with optics about 6 mm in diameter. These, of course, require incisions for insertion which are at least about equal to the diameter of the IOL. These lenses were well suited for the older technique of cataract extraction which required larger incisions, but not well suited for the smaller incisions used in the phacoemulsification technique.

More recently, the soft foldable silicone artificial intraocular lens was developed. This permits a lens with an optical portion about 6 mm in diameter to be folded in half and inserted in the eye. This allows the insertion to be performed through a small incision which is about half as long as the diameter of the unfolded lens. After the folded soft IOL is inserted in the eye, it is permitted to unfold to its full diameter. Such a lens is well suited to be used after the cataract is extracted by the phacoemulsification technique which is done through a small incision.

The techniques of removing a cataract and implanting an IOL through small incisions has a number of advantages for the patient. There is less discomfort from the surgery, faster healing and a more rapid return to normal activities.

The most recent development in cataract surgery includes forming an incision or path to the interior of the eye which differs from previous practice. Instead of forming a "straight line" path to the interior of the eye, the wound is formed tunnel-fashion along three relatively distinct segments. The first is from the outer surface of the eye inward to a depth of about one-half the thickness of the eyeball wall and generally perpendicular to it. The second segment is generally parallel to the interior and exterior eyeball walls and about midway between them. The third segment is also normal to the walls of the eye and enters the eye interior. If viewed in cross section, the wound may be said to have three segments of incision forming a "double-step" path. These wounds are known as "scleral tunnel" incisions. Using a wound of this type for lens implantation results in an advantage for the patient. When the eyeball is slightly pressurized by the surgeon, the wound is self sealing. As a result, sutures can be avoided.

Small incision and tunnel-like wounds have required new instruments and surgical techniques for lens implantation. In the vernacular, such wound configuration requires the surgeon to work in very close quarters.

Several relatively new techniques and instruments have been developed to accommodate wounds of reduced width. For example, the issue of *Ocular Surgery News* of Jul. 15, 1990 discusses a cryo device which is said to freeze a foldable IOL for insertion through a small incision.

Another type of instrument, referred to as a lens injector or "shooter," is shown in catalog sheets published by Staar Surgical Company. The injector rolls a soft lens into a barrel or tube and expels it syringe-style into the interior after the instrument is inserted into the eye. Loss of control is said to be a disadvantage of instruments of this type.

U.S. Pat. No. 4,759,359 (Willis et al.) shows what has come to be known as the phaco-folder. The Willis et al. instrument has a curved trough into which a soft IOL is forced and folded along a diameter by a wire-like end. The trough and the end can be manipulated toward and away from one another.

The instrument shown in U.S. Pat. No. 4,785,810 (Baccala et al.) is similar in concept to that shown in the Willis et al. patent. However, it is illustrated in connection with a soft IOL having an elongate shape and integrally molded tang-like haptics.

These instruments share two disadvantages. One is that the surface of the lens which faces outward upon implantation is interior when the lens is folded. It has been found that in a preferred soft IOL fold, such surface should be exterior. Another is that both instruments include portions (a trough or jaw means as identified respectively in such patents) which increase the thickness of the lens-instrument combination precisely in that region where such an increase is least tolerated.

To put it another way, the Willis et al. and Baccala et al. instruments have portions adjacent to the relatively thick lens center or optical portion when the lens is folded and inserted. This disadvantage is aggravated with IOLs of increasing diopter power since such IOLs are thicker at their center optical portion — and therefore thicker along a diameter fold line.

U.S. Pat. No. 4,844,065 (Faulkner) describes an inserting tool having a pair of relatively straight jaws for holding a circular lens which is folded. Such jaws are bowed outward slightly to accommodate lens curvature and engage the lens along a geometric chord where the lens is somewhat thinner than at its center — but significantly thicker than at the lens edge. The Faulkner tool undesirably adds to the overall thickness of the instrument-lens combination.

A new instrument for implanting a soft IOL which avoids increasing the thickness of the IOL-instrument combination, which can be used with narrow incisions including scleral tunnel incisions and which permits good control of the IOL being released into the eye would be an important advance in the art.

OBJECTS OF THE INVENTION

It is an object of this invention to provide an improved instrument overcoming some of the problems and shortcomings of instruments of the prior art.

Another object of this invention is to provide an improved instrument for implanting a soft IOL which does not increase the maximum aggregate thickness of the instrument-lens combination.

Still another object of this invention is to provide an improved instrument for implanting a soft IOL through a narrower incision.

Yet another object of this invention is to provide an improved instrument for implanting a soft IOL through a scleral tunnel incision.

Another object of this invention is to provide an improved instrument which holds an IOL securely during insertion and releases it in a controlled manner inside the eye.

Another object of this invention is to provide an improved lens implantation instrument which is suitable for packaging with a soft IOL in kit form.

Still another object of this invention is to provide an improved lens implantation instrument which is disposable. These and other important objects will be apparent from the following descriptions and from the drawing.

SUMMARY OF THE INVENTION

The invention is an improvement in a surgical instrument used in cataract surgery to implant an artificial lens in the eye after removal of the cataractous lens. The importance of the invention is underscored by an article in the Oct. 1, 1991 issue of *Ocular Surgery News*. Such article discusses progressive reductions in incision size and states that a "3.5 mm (incision) is state-of-the-art — for now." The improved instrument is of the type having a pair of fingers securely grasping a soft, folded intraocular lens (IOL) therebetween for implantation through a narrow incision in eye tissue. When folded, the IOL has a relatively thick central body and a relatively thin, contoured edge.

In the improved instrument, which minimizes bulk, each finger has a thickness and is shaped to generally conform to the contour of the folded IOL and contact it along the edge. The thickness of each finger is selected so that the combined thickness of the fingers and the edge is no greater than the thickness of the body. The IOL may thereby be implanted through a smaller incision without tearing or unduly gaping the incision.

One exemplary type of foldable IOL is disk-shaped and made of silicone. When unfolded, the contour of the edge of such IOL is circular or substantially so. When folded nominally along a diameter, the contour of the IOL edge is generally the arc of a circle. In a highly preferred embodiment of the improved instrument, each finger is crescent-shaped to generally conform to such contour.

A soft IOL folded for implantation has a degree of "springiness," i.e., a tendency to regain its shape of repose — circular in the example. During implantation of an IOL, it is critical that the ophthalmologist be able to resist that tendency and "control" the IOL through all phases of implantation to avoid inadvertent release. Each finger includes a proximal portion and a distal portion. For improved control, it is preferred that such portions of each finger ar formed toward the proximal and distal portions, respectively, of the other finger. Such arrangement somewhat "closes the gap" between the fingers (irrespective of whether the fingers are closed, open or somewhere in between) and restrains the IOL from "squirting out" or self-ejecting from the instrument in a direction other than that of normal lens release.

In another aspect, each finger includes a segment extending between the proximal and distal portions. The instrument is configured and arranged so that when it is partially open (for imminent release of the IOL into the eye), the space between finger segments is greater than the space between finger proximal and distal portions. Such arrangement is aptly described as "clamshell" opening with the finger segments being analogous to the open edges of the clamshell and the proximal and distal portions being somewhat analogous to the attached edges of the shell even though such portions of a finger are not attached to their counterparts on the other finger.

A folded IOL grasped for implantation presents a "leading" or frontal portion (that portion to first enter the incision) which is rather blunt and therefore more difficult to insert into the incision. And such frontal portion defines a small pocket which may "catch" on tissue. To help overcome these difficulties, each finger includes a guide coacting with that of the other finger and defining a thin extremity. When the IOL is grasped for implantation, the fingers urge the IOL edges toward one another so that the guides are in very close proximity to one another or actually touching. In either instance, the extremity presented by the guides to the incision is relatively thin and the instrument and IOL are streamlined and thus easily inserted.

When implanting an IOL through a narrow incision, it is preferred that the instrument is capable of being manipulated to control and accurately place the IOL while at the same time avoiding significant tearing of eye tissue. In a preferred instrument, each finger is attached to an arm. During IOL release, the arms separate or "spread apart" to have a distance thereacross which, when the IOL is released, is not greater than the width of the incision. Each finger is "offset" somewhat from its supporting arm so that when the IOL is released, the fingers are separated from one another by a distance greater than the distance.

When the new instrument is used to implant an IOL through a scleral tunnel incision — which is significantly longer than a "plunge" incision generally perpendicular to the eyeball walls — the arms are preferably of sufficient length to permit IOL manipulation within the eye while avoiding tearing eye tissue. In a highly preferred instrument, the arms each have a length at least slightly greater than the length of the scleral tunnel entry path.

The instrument fingers may have any of several specific configurations. As an exemplary embodiment (and assuming a disk-shaped IOL with an edge of circular contour), each finger has a crescent-shaped first boundary portion contacting the IOL along the edge. A second boundary portion contacts the body and the boundary portions define a "D" shaped finger. Even though the first boundary portion may be thicker than the second boundary portion, such finger configuration avoids increasing the aggregate IOL-finger thickness. Ease of insertion is maintained.

Soft intraocular lens and instruments used for implanting them are often supplied to the ophthalmologist by different vendors. However, such products lend themselves well to sale by a single vendor in kit form. A kit for implanting an intraocular lens (IOL) includes a soft, foldable IOL and a compatible inventive instrument.

And suppliers and users alike are trending toward disposable instruments. The instrument of the kit may be made at least in part of metal and/or at least in part of plastic and is disposable.

Further details of the invention are set forth below in the detailed description taken in conjunction with the drawing.

DETAILED DESCRIPTIONS OF THE PREFERRED EMBODIMENTS

Figure 1:
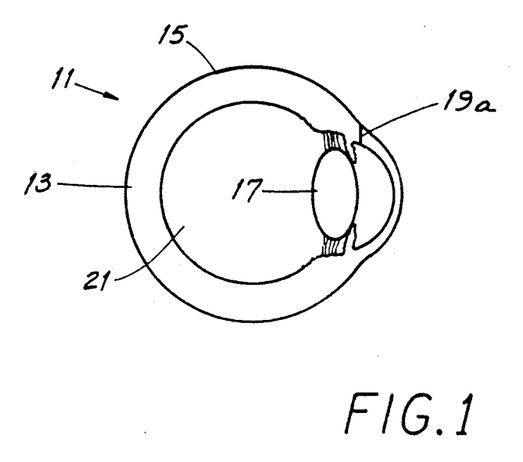
FIGS. 1 and 2 are representative cross-sectional views of a human eye showing different types of incisions used in cataract surgery.
Figure 2:
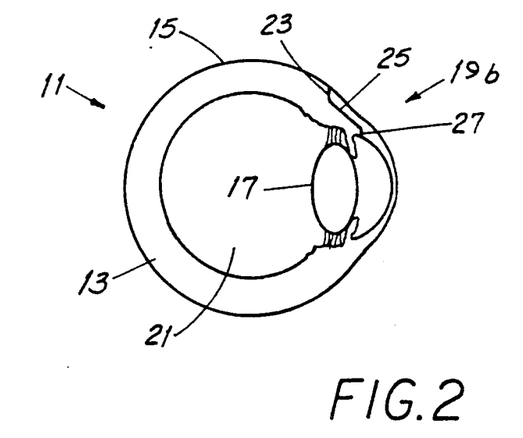

Before describing the inventive instrument 10, readers will find it helpful to become familiar with aspects of the human eye and with various types of soft intraocular lens (IOL) which may be implanted thereinto following removal of the cataractous lens. Referring to FIGS. 1 and 2, the eye 11 has a surrounding, generally spherical wall 13 with an opaque, white outer coat 15 known as the sclera. Near the front of the eye 11 is the capsule 17, a pouch-like portion containing the natural lens and, after its removal, the artificial implant lens.

Entry to the interior of the eye 11 is by an incision 19 through the wall. In FIG. 1, the incision 19a is a "plunge" type wound which is straight. Such incisions, which have been used for a relatively long time, are typically about 10 mm. wide (as measured along the incision "mouth") and even wider. They require several sutures (or "stitches") to close to promote healing and prevent leakage of fluids 21 filling the eye 11. And patient recovery time is lengthened.

The incision 19b shown in FIG. 2 is known as a scleral tunnel incision and has three distinct parts 23, 25, 27. The first part 23, generally normal to and through the sclera 15, penetrates nominally half way through the wall 13. The second part 25 parallels the wall boundaries and the third part 27 enters the eye 11. The width of the parts 23, 25, 27 is quite narrow, on the order of 3-4 mm. Scleral tunnel incisions usually require no sutures, are self-sealing and patient recovery time tends to be shortened. Prevention of leakage of fluids 21 from the eye 11 (both during and after surgery) is important since the pressure created thereby retains eye shape. Excessive leakage causes the eye 11 to lose its shape and, in an extreme case, collapse. While the inventive instrument 10 can be used with either approach described above, it is highly suited for implanting a soft IOL through a narrow incision including a scleral tunnel incision 19b.

Figure 3:
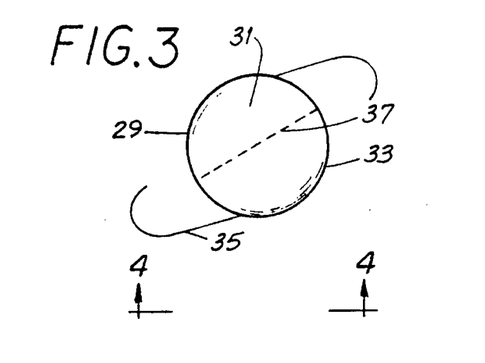
FIG. 3 is a top plan view of one type of soft, foldable intraocular lens.
Figure 4:
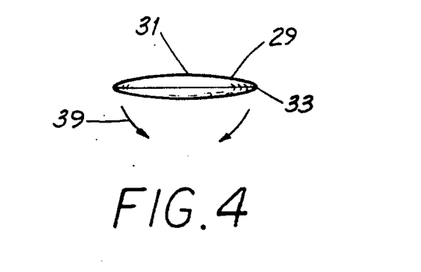
FIG. 4 is an edge view of the lens of FIG. 3 taken along the viewing plane 4—4 thereof.
Figure 5:
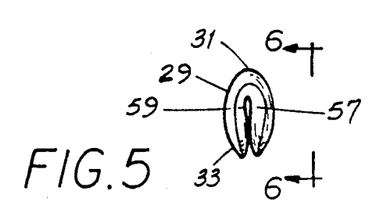
FIG. 5 shows the lens of FIGS. 3 and 4 folded along a diameter.
Figure 6:
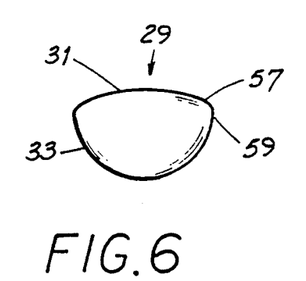
FIG. 6 shows the lens of FIG. 5 taken along the viewing plane 6—6 thereof.

Referring next to FIGS. 3 and 4, one type of disk-like soft, foldable IOL 29 has a optical portion with a relatively thick central body 31 and a thinner, contoured edge 33. In the illustrated IOL, the optic contour is circular. IOLs of this type are about 6-7 mm. in diameter. Attached to the IOL 29 are two wire-like haptics 35 which hold the IOL 29 in position in the eye 11 after implantation. FIGS. 5 and 6 show the IOL of FIGS. 3 and 4 folded along a diameter 37 (as indicated by the arrows 39) for implantation.

Figure 7:
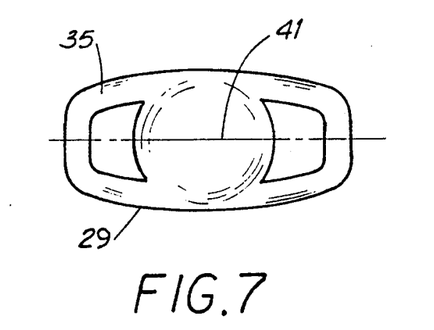
FIG. 7 is a top plan view of another type of soft, foldable intraocular lens.
Figure 8:
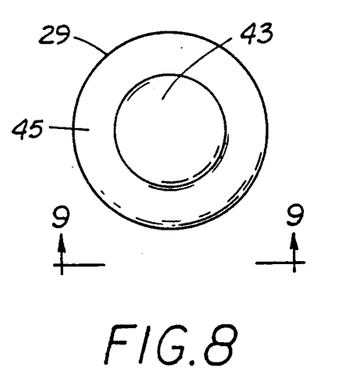
FIG. 8 is a top plan view of yet another type of soft, foldable intraocular lens.
Figure 9:
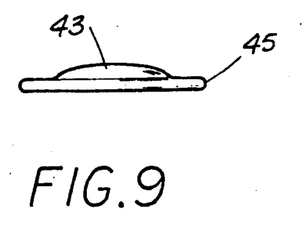
FIG. 9 is an edge view of the lens of FIG. 8 taken along the viewing plane 9—9 thereof.
Figure 10:
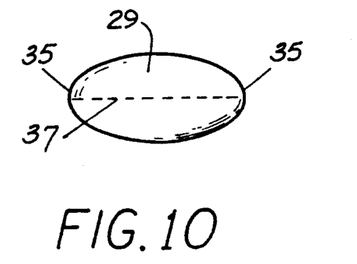
FIG. 10 is a top plan view of still another type of soft, foldable intraocular lens of ovoid form.

FIG. 7 shows another type of soft foldable IOL 29, the haptic contour of which is "curved rectangular." This IOL has integrally-molded loop haptics 35 and is folded along the long axis 41 when prepared for implantation. Yet another type of IOL 29 is shown in FIGS. 8 and 9 and has a thicker optical portion 43, a thinner haptic edge 45 and an edge contour which is circular. Such IOL 29 tends to resemble a fried egg in appearance. Still another type of IOL 29 (not yet available insofar as is known) is shown in FIG. 10 and has an ovoid optic and an elliptical optical edge contour.

Lens 29 of the foregoing types have been implanted or proposed for implantation and the lens 29 shown in FIGS. 3-6 has found great favor with many ophthalmologists. A common material for making foldable IOLs 29 is silicone.

Figure 11:
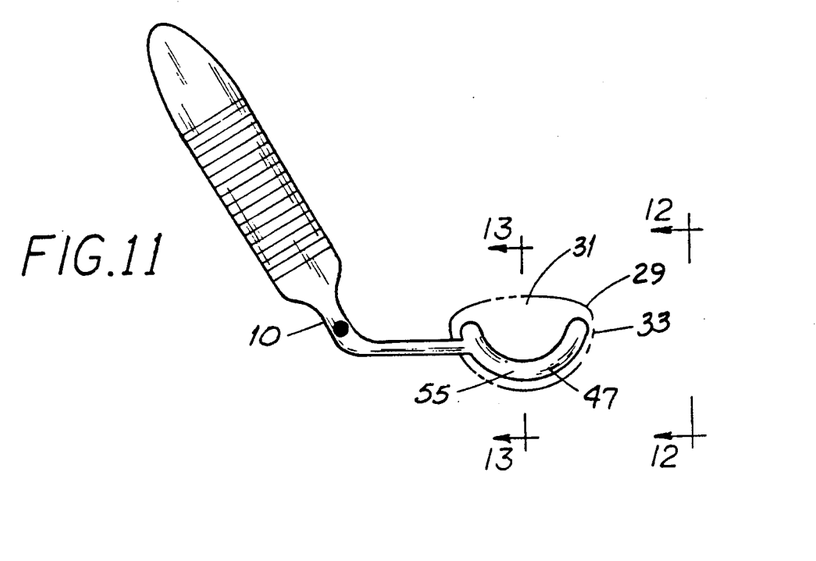
FIG. 11 is a side elevation view of the improved instrument shown in connection with a folded lens represented in dashed outline.
Figure 12:
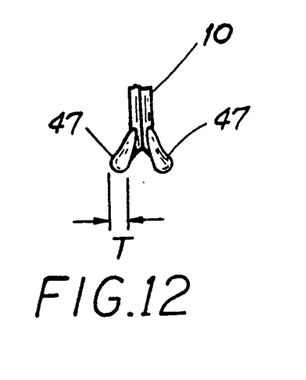
FIG. 12 is an end elevation view of the instrument of FIG. 11 taken along the viewing plane 12—12 thereof with part broken away.
Figure 13:
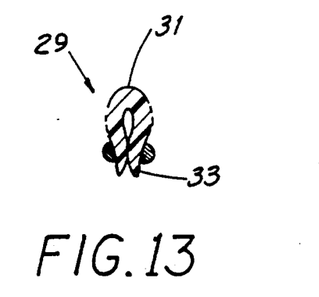
FIG. 13 is a representative sectional view of the instrument and lens of FIG. 11 taken along the viewing plane 13—13 thereof.

Referring next to FIGS. 11-13, the improved instrument 10 is of the type having a pair of fingers 47 grasping a soft, folded intraocular lens 29 (IOL) therebetween for implantation through a narrow incision (like incision 19b) in eye tissue. When folded, the IOL 29 has a relatively thick central body 31 and a relatively thin, contoured edge 33.

In the improved instrument 10, each finger 47 has a thickness "T" and is shaped to generally conform to the contour of the folded IOL 29 and contact it along the optics edge 33. The thickness of each finger 47 is selected so that when the IOL 29 is folded and grasped by the instrument 10, the combined thickness of the fingers 47 and the edge 33 is no greater than the thickness of the body 31. This relationship is illustrated in FIGS. 11 and 13. The IOL 29 may thereby be implanted through a smaller incision without tearing or unduly gaping the incision 19. Minimization of gaping is important in preventing leakage of the fluid 21 and possible distortion or collapse of the eye 11.

When the illustrated IOL 29 is folded nominally along a diameter 37, the contour of the IOLs optic edge 33 is generally the arc of a circle. In a highly preferred embodiment of the improved instrument 10, each finger 47 is crescent-shaped to generally conform to such contour.

An IOL 29 folded for implantation has a degree of "springiness," i.e., a tendency to regain its shape of repose — circular in the case of the IOL 29 shown in FIGS. 3-6, 8, 9, 11, 13. During implantation of an IOL 29, it is critical that the ophthalmologist be able to resist that tendency and "control" the IOL 29 through all phases of implantation to avoid inadvertent release. To that end and in another embodiment shown in FIGS. 14 and 15, each finger 47 includes a proximal portion 49 and a distal portion 51. For improved control, it is preferred that such portions 49, 51 of each finger 47 are formed or "bent" toward the proximal and distal portions 49, 51, respectively, of the other finger 47. Such arrangement somewhat "closes the gap 53" between the fingers 47 (irrespective of whether the fingers 47 are closed, open or somewhere in between) and restrains the IOL 29 from "squirting out" or self-ejecting from the instrument 10 in a direction other than that of normal lens release.

Figure 14:
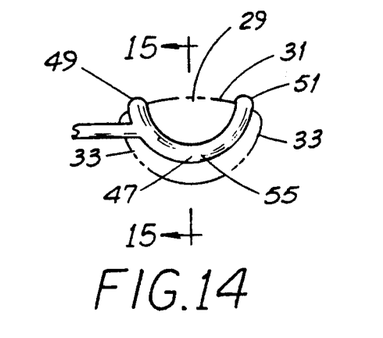
FIG. 14 is a side elevation view of another embodiment of the instrument of FIG. 11 with parts broken away and with a folded lens represented in dotted outline.
Figure 15:
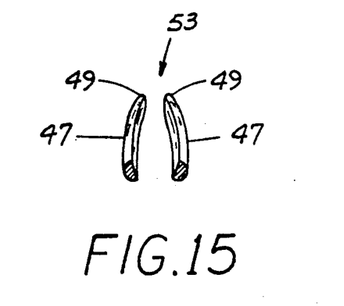
FIG. 15 is a representative sectional view of the instrument of FIG. 14 taken along the viewing plane 15—15 thereof.

Comparing FIGS. 11 and 14, FIG. 14 may suggest to the casual reader that the portions 49, 51 of the fingers 47 are in contact with the relatively thick body 31 and that when viewed in cross-section the aggregate thickness of the fingers 47 and the IOL 29 is greater than that of the IOL body 31 alone. Such is not the case. It is to be appreciated that when the IOL 29 of FIGS. 3-6, 14, 16 is folded and grasped by the fingers 47 as illustrated in FIG. 14, and 15 the fingers 47 contact the IOL 29 along the thin edge 33, not on the thicker body 31, and there is no increase in overall thickness as viewed in cross section. And the foregoing is true with respect to other types of IOLs 29 illustrated in the drawing.

Figure 16:
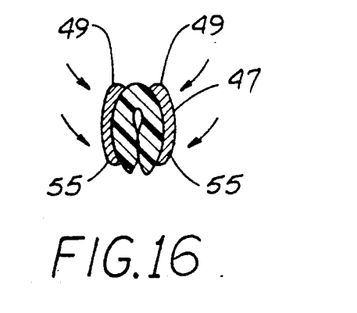
FIGS. 16 and 17 are representative views showing "clamshell" closing and opening of the fingers of the instrument.
Figure 17:
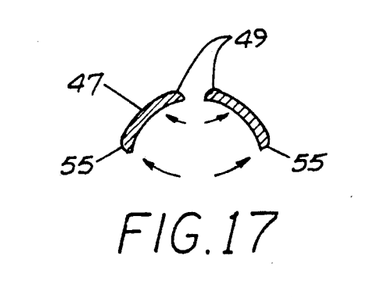

Referring additionally to FIGS. 16 and 17 and in another aspect of the inventive instrument 10, each finger 47 includes a segment 55 extending between and bounded by the proximal and distal portions 49, 51. When the instrument 10 partially open, the corresponding portions 49 or 51 of the fingers 47 have a space between them as do the segments 55. The improved instrument is configured and arranged so that when more fully open, the space between segments 55 is greater than either of the spaces between the corresponding portions 49 or 51, thereby providing controlled release of the IOL.

Such arrangement is aptly described as "clamshell" opening with the finger segments 55 being analogous to the open edges of the clamshell and the proximal and distal portions 49, 51 being somewhat analogous to the attached edges of the shell even though such portions 49, 51 are not attached to one another.

As best seen in FIGS. 5 and 6, a folded IOL 29 grasped for implantation presents a "leading" or frontal portion 57 (that portion to first enter the incision 19) which is rather blunt and therefore more difficult to insert into the incision 19. Such frontal portion 57 defines a small pocket 59 which, because of its appearance, is sometimes referred to as having a "fish mouth" shape. Such pocket 59 can also obstruct easy insertion.

Figure 18:
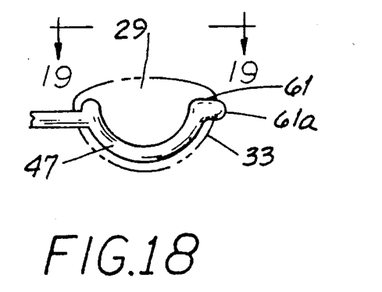
FIG. 18 is a side elevation view of yet another embodiment of the instrument of FIG. 11 taken from the same perspective as that of FIG. 11 and with parts broken away and a folded lens in dashed outline.
Figure 19:
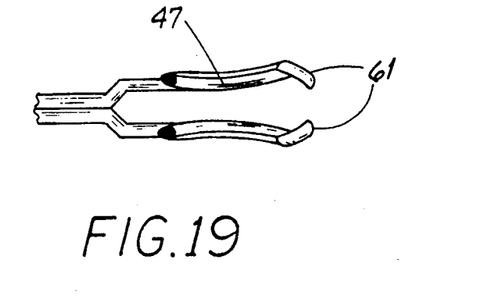
FIG. 19 is a top plan view of the instrument of FIG. 18 taken along the viewing plane 19—19 thereof.

Referring to FIGS. 18 and 19, to help overcome insertion difficulties arising therefrom, each finger 47 includes a guide 61 coacting with that of the other finger 47 and defining a thin leading edge or extension 61a. When the IOL 29 is grasped for implantation, the guides 61 urge the forward IOL edges 33 toward one another so that the guides 61 are in very close proximity to one another or actually touching. In either instance, the extension 61a presented to the incision 19 by the guides 61 is relatively thin and the instrument 10 and IOL 29 are easily inserted. Such configuration also helps avoid catching the instrument 10 or the IOL 29 on the incision 19 or interior structures of the eye 11.

Figure 20:
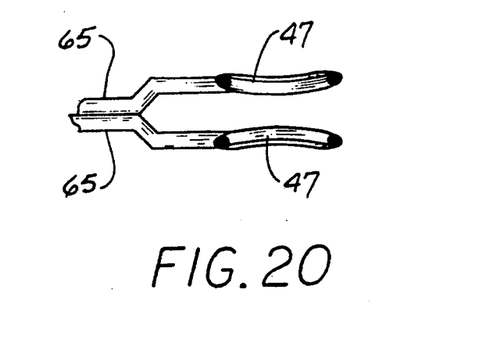
FIG. 20 is a top plan view of another embodiment of the invention with parts broken away.
Figure 21:
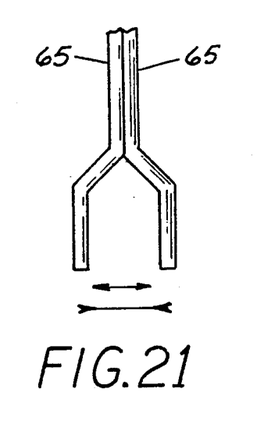
FIG. 21 is a representative top plan view of the instrument showing arm configuration and with the instrument in a lens-grasping position.
Figure 22:
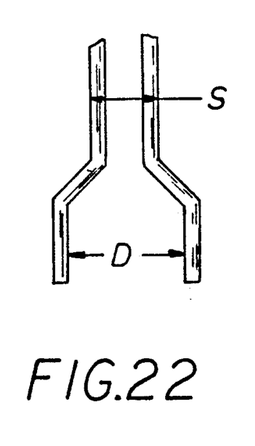
FIG. 22 is a representative top plan view of the instrument of FIG. 21 with the instrument in a lens-releasing position.

When implanting an IOL 29 through a narrow incision 19, it is preferred that the instrument 10 is capable of being manipulated to control and accurately place the IOL 29 while at the same time avoiding significant tearing of eye tissue. Referring now to FIGS. 20-22 in a preferred instrument 10, each finger 47 is attached to an arm 65. During IOL release, the arms 65 separate or "spread apart" as shown in FIG. 22 to have a span "S" thereacross which, when the IOL 29 is released, is not greater than the width of the incision 19.

In current surgical practice, a maximum span of about 3-4 mm. is indicated. However, the aforementioned relationship is irrespective of incision width. Each finger 47 is "offset" somewhat from its supporting arm 65 so that for positive IOL release, the fingers 47 are separated from one another by a distance "D" which is greater than the span "S." It is to be appreciated that while the arms 65 are within the incision 19 (such as incision 19b), the fingers 47 are interior the eye 11 at the item of IOL release. Therefore, the spacing of the fingers 47 is not limited to incision width.

When the new instrument 10 is used to implant an IOL 29 through a scleral tunnel incision 19b — which has a significantly greater path length than the path of a "plunge" incision 19a — the arms 65 are preferably of sufficient length to permit IOL manipulation within the eye 11 while avoiding tearing eye tissue. In a highly preferred instrument 10, the arms 65 each have a length at least slightly greater than the length of the tunnel incision path 19b.

Figure 23:
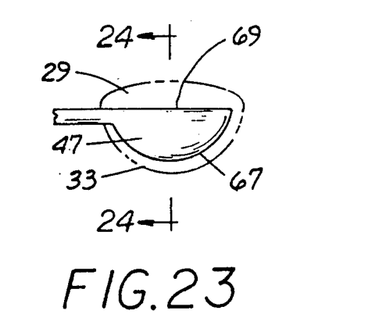
FIGS. 23 is a side elevation view of yet another embodiment of the instrument with parts broken away and showing a folded lens in dashed outline.
Figure 24:
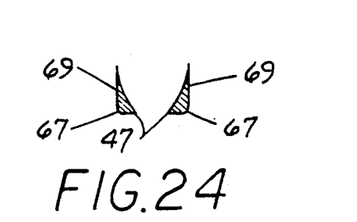
FIG. 24 is an end elevation view of the instrument of FIG. 23 taken along the viewing plane 24—24 thereof.

The instrument fingers 47 may have any of several specific configurations. Some are shown in FIGS. 11, 14, 19 and 20. As an exemplary embodiment (and assuming a disk-shaped IOL 29 optic with an edge 53 of circular contour), FIG. 23 shows each finger 47 to have a crescent-shaped first boundary portion 67 contacting the IOL 29 along the edge 33. A second boundary portion 69 contacts the thicker central body 31 and the boundary portions 67, 69 define a finger 47 shaped like the letter "D" on its side. Even though the first boundary portion 67 may be thicker than the second boundary portion 69 as shown in FIG. 24, the first portion 67 contacts the IOL 29 at its thinnest part along the edge 33. Therefore, such finger configuration avoids increasing the aggregate IOL-finger thickness and ease of insertion is maintained.

Soft intraocular lens 29 and instruments used for implanting them are often supplied to the ophthalmologist by different vendors. Such IOLs 29 are usually packaged in a small cassette 71 while instruments are packaged in a box 73 having a shape-conforming cavity. Such exemplary packaging is shown in FIG. 25.

Figure 25:
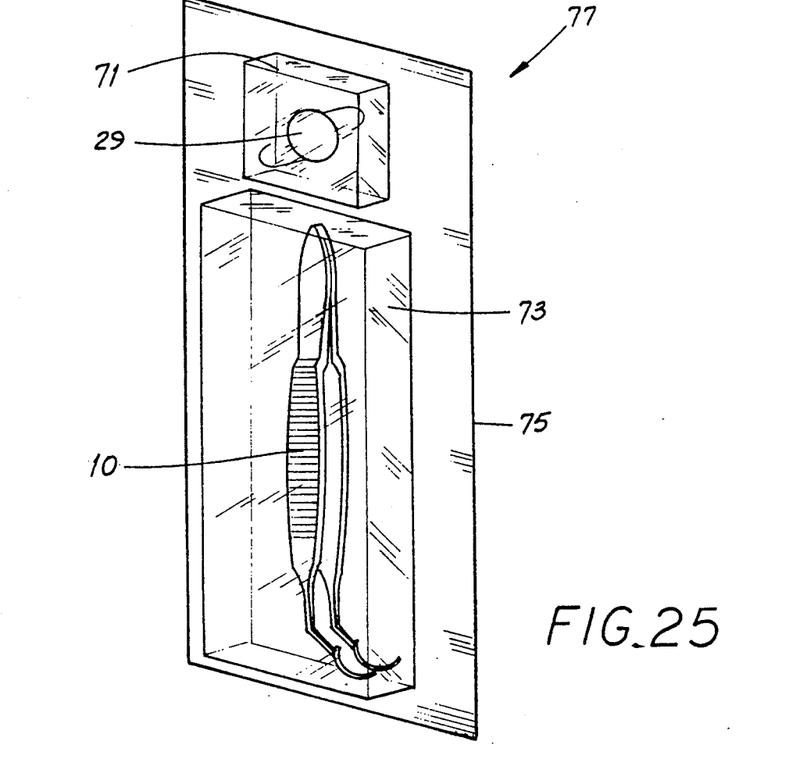
FIG. 25 is a representative perspective view of a lens implant kit including the inventive instrument and a soft, foldable intraocular lens.

However, such products lend themselves well to sale by a single vendor in kit form and FIG. 25 also shows a kit-like sealed plastic bag 75 containing both products 10, 29. Of course, any of several possible types of kit packaging could be used.

A kit 77 for implanting an intraocular lens (IOL) includes a soft, foldable IOL and a compatible instrument 10. The IOL 29 and instrument 10 are preferably configured as described above.

And suppliers and users alike are trending toward disposable instruments. The instrument 10 of the kit 77 may be made at least in part of metal and/or at least in part of plastic and be disposable. As used herein, the term "plastic" includes plastic, reinforced glass, fiber-reinforced graphite and other non-metallic materials suitable for use in making an instrument 10 of the foregoing type.

Figure 26:
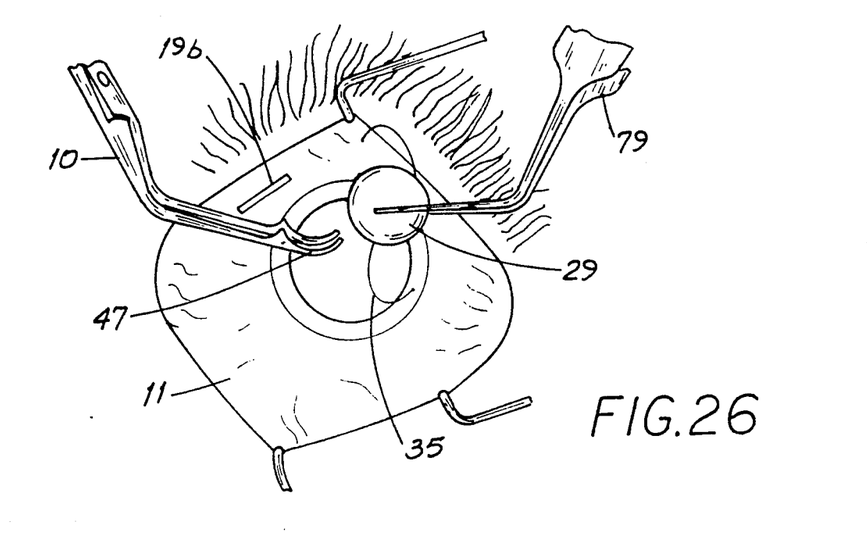
FIG. 26-30 are sequential views showing how the inventive instrument is used to fold and grasp a lens and insert such lens in an incision.
Figure 27:
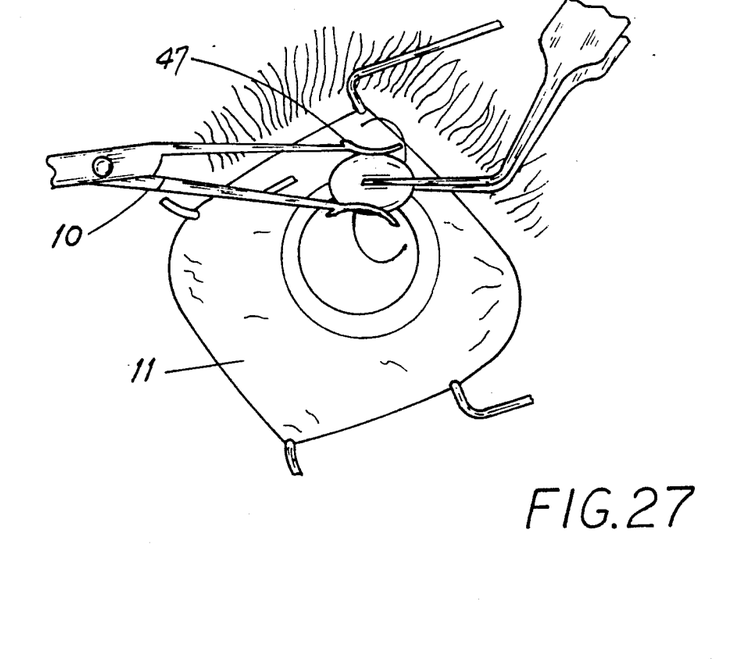
Figure 28:
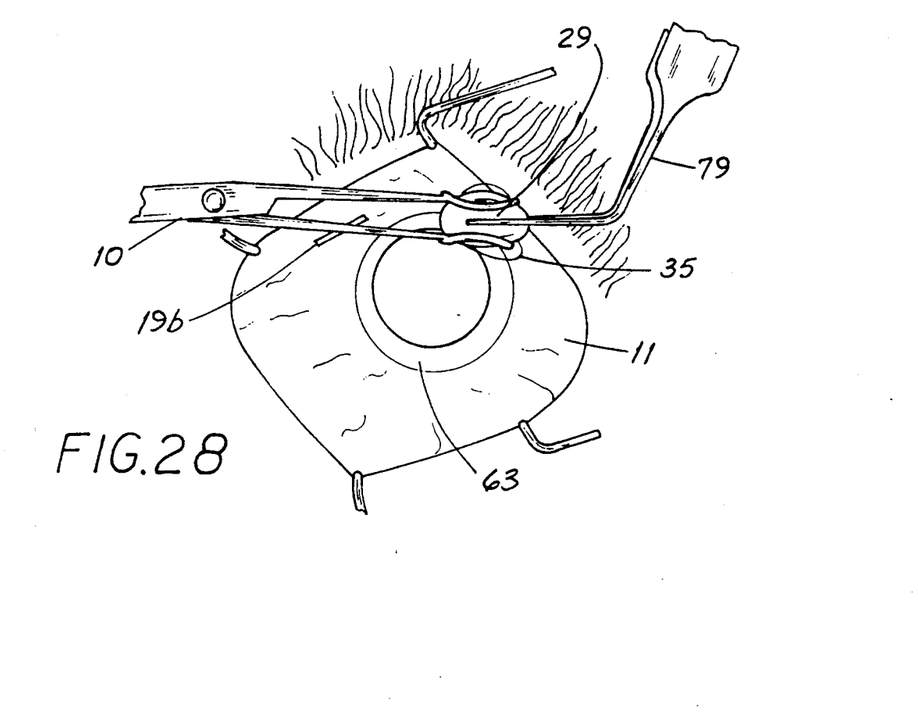
Figure 29:
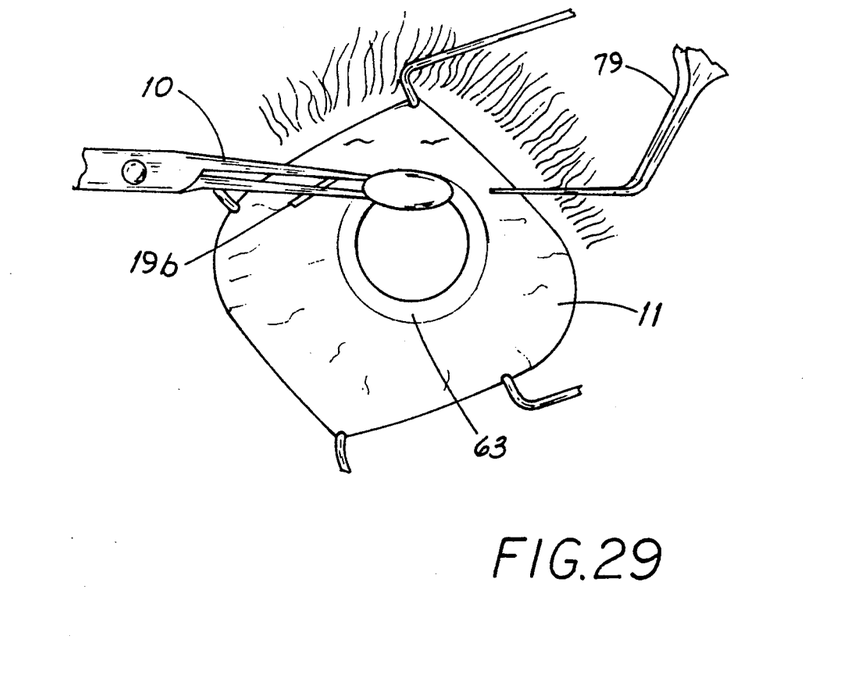
Figure 30:
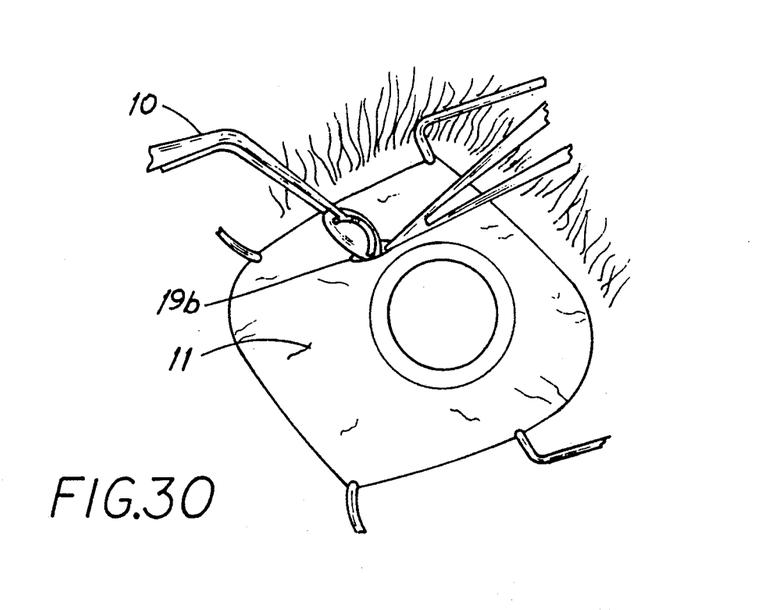

FIGS. 26-30 are depictions of photographs taken during cataract surgery testing the improved instrument 10. To prepare the IOL 29 for implantation, it is grasped along a diameter 37 using a fine-tipped, non-toothed forceps 79 as shown in FIG. 26. The fingers 47 of the instrument 10 are then urged downward on the IOL 29 as shown in FIG. 27 and 28 to grasp and fold the IOL 29. After folding, the haptics 35 may be "tucked" into the IOL 29 as in FIG. 28 so they do not snag the incision 19b during implantation. Once the IOL 29 is so prepared and grasped, the instrument 10 (with captured IOL 29) is rotated onto its side as shown in FIG. 30 and inserted through the incision 19b. Once the fingers 27 and IOL 29 are inside the eye 11, the instrument 10 is returned to the orientation shown in FIG. 29 and the IOL 29 controllably placed in the eye 11. The surface of the IOL 29 toward the viewer (away from the patient) in FIGS. 27-29 is that which is outward (toward the eye anterior) when the IOL 29 is implanted. It is to be appreciated that implantation instruments of other types have been used in the past and the described folding and grasping techniques are known.

While the principles of this invention have been described in connection with specific embodiments, it should be understood clearly that these descriptions are made only by way of example and are not intended to limit the scope of the invention.

What is claimed:

1. In combination, (a) a soft foldable, convex intraocular lens (IOL) having a relatively thick central optical portion and a relatively thin peripheral edge portion, and (b) a surgical instrument having a pair of fingers for folding the lens in half and holding the lens, the fingers being movable between an open position and a closed, lens-holding position and wherein: said lens, when folded, having a doubled-over central optical portion and doubled-over peripheral edge portions, each finger has a generally concave surface and the concave surfaces of both fingers face substantially the same direction when the fingers rae in the lens-holding position; each finger has a lens-contacting surface generally separate from the concave surface;

said instrument configured to hold said lens in a folded configuration between said fingers such that each finger contacts the lens along one of the doubled-layer edge portions and extends partly around the doubled-over central optical portion; and, the combined thickness of the fingers and the doubled-over lens' edge portions therebetween is not greater than the doubled-over thickness of the central optical portion, whereby the lens may be implanted through a small incision.

2. The combination of claim 1 wherein when the lens is unfolded, the peripheral edge portion is generally circular and each instrument finger is crescent-shaped.

3. The combination of claim 1 wherein each finger includes proximal and distal end portions, the proximal portion of each finger is bent toward the proximal portion of the other finger and the distal portion of each finger is bent toward the distal portion of the other finger thereby aiding in restraining the lens from self-ejecting from the instrument.

4. The improved instrument of claim 1 wherein each finger includes a guide coacting with the guide of the other finger and defining a thin extension whereby the instrument and IOL are easily inserted into the incision.

5. The combinations of claim 1 wherein; when the fingers hold the folded lens there between,
   the fingers are separated from one another by a distance;
   each finger is attached to an arm; and,
   the arms define a span thereacross which is less than the span defined across the fingers and the lens held there between, whereby an IOL is more easily released after passing through a small incision.

6. The combination of claim 1 wherein each finger has a first boundary portion away from the doubled-over central optical portion, a second boundary portion toward the double-over central optical portion and in cross-section, the second boundary portion is thinner than the first boundary portion whereby when the instrument holds the lens, the overall thickness of the fingers and the lens' doubled-over edge portion is not greater than the thickness of the doubled-over central optical portion of the folded lens.

7. The kit of claim 5 wherein the instrument is made at least in part of metal and is disposable.

8. The kit of claim 5 wherein the instrument is made at least in part of plastic and is disposable.

9. A kit for implanting an intraocular lens (IOL) including:
   a foldable soft convex IOL having a fold axis, a relatively thick central optical portion and a relatively thin edge and wherein;
   when unfolded the lens has a perimeter shape defined by the edge;
   when folded in half along the fold axis for insertion into the eye, the lens is doubled over upon itself, thereby forming edge portions which are half portions of the edge perimeter of the unfolded lens and also forming a doubled-over central optical portion,
   and the kit further includes:
      an IOL-implantation instrument having a pair of fingers for grasping the lens in a folded configuration, each finger has a thickness and a curvilinear shape generally conforming to the shape of one of the edge portions of the edge perimeter, with the lens in its folded configuration held between the fingers of the implantation instrument,
      each finger grasps the folded lens along one of the edge portions of the edge perimeter; and,
      the combined thickness of the fingers and the lens' doubled-over edge portions therebetween is not greater than the thickness of the doubled-over central optical portion,
   whereby the IOL may be implanted through a small incision.

10. In combination, a surgical instrument and a foldable soft, convex intraocular lens having a relatively thick central optical portion, a relatively thin peripheral edge portion and a folding axis, the instrument including a pair of fingers for folding the lens in half along the axis and holding the lens and wherein:
   when folded in half along the folding axis for insertion into the eye, the lens is doubled over upon itself forming doubled-over edge portions and a doubled-over central optical portion, the instrument improvement wherein with said lens in its folded configuration and held between said fingers:
      each finger has a first boundary portion away from the folding axis of the lens and extending along one of the lens' doubled-over edge portions;
      each finger has a second boundary portion toward the folding axis of the lens; and,
      in cross-section, the second boundary portion is thinner than the first boundary portion,
   whereby when the instrument holds the lens, the overall thickness of the fingers and the lens' doubled-over edge portions there between is not greater than the thickness of the doubled-over central optical portion of the lens.

11. In combination, (a) a soft, folded convex intraocular lens (IOL) having a relatively thick doubled-over central optical portion and relatively thin doubled-over edge portions, and (b) a surgical instrument having a pair of fingers for grasping the lens along the lens edge and wherein:
   each finger has a thickness and a curvilinear shape generally conforming to the shape of one of the lens' doubled-over edge portions
   each finger grasping the folded lens along one of the lens' doubled-over edge portions; and,
   the combined thickness of the fingers and the doubled-over edge portions there between is not greater than the folded thickness of the doubled-over central optical portion;
and wherein:
   each finger has a first boundary portion away from the central optical portion, a second boundary portion toward the central optical portion and in cross-section, the second boundary portion is thinner than the first boundary portion,
whereby the lens is securely grasped and may be implanted through a small incision.

12. A kit for implanting an intraocular lens (IOL) including:
   a foldable soft convex IOL having a fold axis, a relatively thick central optical portion and a relatively thin edge portion and wherein;
   when unfolded, the lens has a perimeter shape defined by the edge portion;
   when folded in half along the axis for insertion into the eye, the lens is doubled over upon itself, thereby forming edge portions which are half portions of the edge perimeter of the unfolded lens,
   and the kit further includes:
      a disposable IOL-implantation instrument made at least in part of metal and having a pair of fingers for grasping the lens, each finger has a thickness and a curvilinear shape generally conforming to the shape of one of the edge portions of the edge perimeter,
      each finger grasping the lens in a folded configuration along one of the edge portions of the edge perimeter; and,
      the combined thickness of the fingers and the lens' edge portions therebetween is not greater than the folded thickness of the central optical portion,
   whereby the IOL may be implanted through a small incision.

13. A kit for implanting an intraocular lens (IOL) including:
   a foldable soft convex IOL having a fold axis, a relatively thick central optical portion and a relatively thin edge portion and wherein;
   when unfolded, the lens has a perimeter shape defined by the edge portion;
   when folded in half along the fold axis for insertion into the eye, the lens is doubled over upon itself, thereby forming edge portions which are half portions of the edge perimeter of the unfolded lens,
   and the kit further includes:
      a disposable IOL-implantation instrument made at least in part of plastic and having a pair of fingers for grasping the lens, each finger has a thickness and a curvilinear shape generally conforming to the shape of a one of the edge portions of the perimeter, each finger grasping the lens in a folded configuration along one of the edge portions of the edge perimeter; and the combined thickness of the fingers and the lens' edge portions therebetween is not greater than the folded thickness of the central optical portion, whereby the IOL may be implanted through a small incision.

* * * * *

UNITED STATES PATENT AND TRADEMARK OFFICE
CERTIFICATE OF CORRECTION

PATENT NO. : 5,178,622
DATED : January 12, 1993
INVENTOR(S) : Robert H. Lehner, II It is certified that error appears in the above-identified patent and that said Letters Patent is hereby corrected as shown below:

In column 10, line 57, delete "improved instrument" and insert --combination--.

In column 11, line 13, delete "kit" and insert --combination--

In column 11, line 15, delete "kit" and insert --combination--.

Signed and Sealed this

Twenty-first Day of December, 1993

Attest:

BRUCE LEHMAN

*Attesting Officer*  *Commissioner of Patents and Trademarks*